United States Patent [19]
Marshall

[11] Patent Number: 6,052,625
[45] Date of Patent: Apr. 18, 2000

[54] EXTRACTABLE IMPLANTABLE MEDICAL LEAD

[75] Inventor: Mark T. Marshall, Forest Lake, Minn.

[73] Assignee: Medtronic, Inc., Minneapolis, Minn.

[21] Appl. No.: 09/188,859

[22] Filed: Nov. 9, 1998

[51] Int. Cl.[7] ................................................ A61N 1/05
[52] U.S. Cl. ................................................ 607/122; 607/126
[58] Field of Search .................................... 607/116, 119, 607/122, 126–128; 600/373–375

[56] References Cited

U.S. PATENT DOCUMENTS

| | | |
|---|---|---|
| 4,161,952 | 7/1979 | Kinney et al. . |
| 4,409,994 | 10/1983 | Doring ..................................... 607/126 |
| 4,506,680 | 3/1985 | Stokes . |
| 4,572,605 | 2/1986 | Hess . |
| 4,934,049 | 6/1990 | Kiekhafer et al. . |
| 4,944,088 | 7/1990 | Doan et al. . |
| 4,972,848 | 11/1990 | DiDominico et al. . |
| 5,115,818 | 5/1992 | Holleman et al. . |
| 5,231,996 | 8/1993 | Bardy et al. . |
| 5,246,014 | 9/1993 | Williams et al. . |
| 5,364,662 | 11/1994 | Domenico et al. . |
| 5,584,873 | 12/1996 | Shoberg et al. . |
| 5,676,694 | 10/1997 | Boser et al. . |
| 5,760,341 | 6/1998 | Laske et al. . |
| 5,782,900 | 7/1998 | de le Rama et al. .................... 607/122 |

*Primary Examiner*—Jeffrey R. Jastrzab
*Assistant Examiner*—George R. Evanisko
*Attorney, Agent, or Firm*—Reed A. Duthler; Harold R. Patton

[57] ABSTRACT

A medical electrical lead with a tip-ring assembly optimized to resist damage during extraction. The lead includes an elongated plastic tube and at least two elongated conductors mounted in the plastic tube. A tip-ring assembly is mounted to the distal end of the tube, the tip-ring assembly including a ring electrode coupled to one of the conductors, a tip electrode located distal to the ring electrode and coupled to another of the conductors and two molded plastic components separately fabricated of a plastic harder than the plastic tube, adhered to one another and together defining a circumferential groove in which the ring electrode is located and mechanically coupled to the tip electrode. The tip electrode may be provided with a proximally extending electrode shank covered by a tine sleeve which is fabricated of a plastic softer than the molded plastic components and is adhered to more distally located molded plastic component. The more distally located molded plastic component preferably overlaps the electrode shank to provide a stronger structure.

4 Claims, 8 Drawing Sheets

EXTRACTABLE IMPLANTABLE MEDICAL LEAD

BACKGROUND OF THE INVENTION

This invention relates generally to medical leads and more particularly to implantable cardiac leads.

In the context of implantable leads, and particularly in the context of implantable cardiac leads, there is often a need to remove a lead after it has been implanted in a patient's body for some period of time. In conjunction with lead removal, it is often necessary to apply traction to the lead, in order to pull it free from tissue adhering thereto. It has therefore been recognized for some time that a reinforcement of some type, extending along the lead body would be beneficial, in order to prevent breakage or partial disassembly of the lead during removal. For example, in U.S. Pat. No. 5,231,996 issued to Bardy et al., a variety of reinforcement mechanisms are disclosed, including cords, filaments, braids, and the like.

More recently, in the context of implantable cardiac leads, the use of cabled or stranded conductors in place of the previously more commonly employed coiled conductors has become more popular. These cabled or stranded conductors, such as disclosed in U.S. Pat. No. 5,584,873 issued to Shoberg et al., U.S. Pat. No. 5,760,341 issued to Laske et al. and U.S. Pat. No. 5,246,014 issued to Williams et al. inherently provide an increased tensile strength lead, at least along the segment between the point at which the stranded or cabled conductor is coupled to an electrode and the point at which the conductor is coupled to an electrical connector at the proximal end of the lead. While this new conductor inherently provides a lead of enhanced tensile strength, in most transvenous cardiac pacing leads employing cabled or stranded conductors, the conductor which extends to the distal-most portion of the lead is still a coiled conductor in order to permit passage of a stylet. This distal-most portion of the lead, particularly in the context of leads employing tines or other passive fixation mechanisms, is the portion of the lead to be most likely to be firmly embedded in fibrous tissue. It is therefore desirable that this portion of the lead in particular should be capable of withstanding high tensile forces without breakage.

SUMMARY OF THE INVENTION

The lead disclosed in the present application is particularly designed to reduce problems associated with extraction after implant. In order to accomplish this goal, the lead is provided with three structural features, each directed particularly to providing a lead which is easier to extract and less likely to be damaged during the extraction process.

The first feature of the lead is an improved tip-ring assembly, extending from the tip or distal electrode and including the associated ring electrode located proximal thereto. In particular, the tip-ring assembly is adapted for use in conjunction with electrodes employing passive fixation mechanisms such as tines, in which the tip electrode is fixedly mounted with respect to the lead body, rather than advanceable from the lead body as in the context of a screw-in lead. In order to enhance the durability of the lead during the extraction, the tip-ring assembly is fabricated of three molded plastic components, two of which are fabricated of a relatively rigid plastic, harder than that typically employed in the segment between the tip and ring electrode in bipolar leads employing passive fixation mechanisms. The plastic components are configured to provide a mechanical interlock between the tip electrode and the ring electrode when assembled, and are additionally bonded to plastic insulative tubes or coatings covering coiled and/or cabled conductors extending to the tip-ring assembly area.

In particular, the tip-ring assembly includes a tine sleeve having a central lumen into which a proximal extending shank portion of the tip electrode is inserted, a tip-ring spacer component, adapted to be glued to the proximal end of the tine sleeve and a ring-coil spacer component, adapted to be glued to the tip-ring spacer component, and around which a ring electrode may be located. The ring-coil and tip-ring spacer components together define a circumferential groove dimensioned to receive and retain the ring electrode. The distal end of the tip-ring spacer is configured to overlap the proximal end of the electrode shank located within the tine sheath, so that an generally rigid assembly is provided extending from the distal or tip electrode through and including the ring electrode of the lead. The ring electrode is coupled to a stranded or cabled conductor which extends to the proximal end of the lead, which together with the components of the tip-ring assembly provide a first mechanism for transmission of tensile force applied to the proximal end of the lead all the way to the distal or tip electrode.

A second feature of the invention relates to the provision of insulative coatings or tubings covering these strand and/or coiled conductors employed in the lead which have been treated to enhance their bonding performance, so that they may usefully be adhered to molded or extruded plastic components at either end of the lead, further providing for an additional mechanism of transmission of tensile force along the lead body. In this context, the conductor coupled to the tip electrode may be a coiled conductor surrounded by a heat shrink tube of polytetrafloroethelene (PTFE) which has been treated by etching or otherwise to enhance the ability to bond thereto. The distal end of the heat shrink tube may be bonded adhesively to one or more of the tine sleeve, the ring-coil spacer component and the tip-ring spacer component and to the connector assembly at the proximal end of the lead. The heat shrink PTFE tubing in conjunction with the associated coiled conductor and the adhesive bonds at the proximal and distal end of the lead provide a second mechanism for providing enhanced tensile strength extending along the entire length of the lead. The cabled conductor coupled to the ring electrode referred to above may correspondingly be provided with a plastic insulative coating, treated to improve adhesion. For example, the cabled conductor may be provided with a coating of ETFE, modified by plasma coating using silane gas to provide for increased bonding capabilities. The insulative coating on the cabled conductor may likewise be bonded to plastic components located at the proximal and distal ends of the lead, in turn allowing for distribution of tensile forces between the mechanical joints coupling the cabled conductor to the metal electrode and electrical connector components located at the distal and proximal ends of the leads respectively and adhesive bonds between the insulation and associated nearby plastic parts. The insulation may, for example be bonded to the molded parts associated with the tip-ring spacer and the connector assembly and/or to the extruded plastic tubing making up the lead body. By this mechanism, the ability of the cabled conductors to transmit tensile forces from the proximal end of the lead to the distal portion of the lead without damage to the lead is further enhanced. The improved bonding characteristics provided by surface treatment of the isulative coatings and/or tubes also assist in maintaining effective seals against fluid intrusion and migration within the lead body.

A third feature of the lead intended to improve its extraction characteristics is directed specifically to leads of the type employing elongated coil electrodes, for example as in implantable cardioversion and defibrillation leads. In some leads of this type, the coil is molded into the lead body, such as in U.S. Pat. No. 4,161,952 issued to Kinney et al. However, a simpler alternative construction mechanism is t simply mount coil electrodes fabricated of single or multifilar coils around the exterior of an extruded tubular lead body. Such coil electrodes are disclosed in U.S. Pat. No. 4,934,049 issued to Kiekhafer et al., U.S. Pat. No. 5,115,818 issued to Holleman et al. and U.S. Pat. No. 5,676,694 issued to Boser et al, all incorporated herein by reference in their entireties. Experience has shown that discontinuities in lead diameter associated with the proximal and distal ends of such coil electrodes can complicate removal of the lead from its overlying fibrous sheath. This is true whether the removal is accomplished by attempting to remove the fibrous sheath prior to extraction lead or whether the lead is to be simply pulled through the fibrous sheath. According to this feature of the invention, tubing is provided overlying the extruded lead body intermediate the coil electrodes, if there is more than one such electrode and intermediate the proximal end of the most proximal coil electrode and the connector assembly located at the proximal end of the lead. In this fashion, a lead can be provided which is essentially isodiametric along the length of the lead body to the distal end of the distal-most coil electrode, which lead can be fabricated of extruded multi-lumen tubing and which does not require molding the coil electrode into the lead body. Preferably, if a ring electrode is located distal to the distal-most coil electrode, it too is configured to be essentially isodiametric to the electrode coil and to the lead body or other plastic component separating the distal end of the distal-most coiled conductor and the ring electrode. This particular construction mechanism is especially convenient in the context of a lead of the type employing an extruded multi-lumen tubular lead body, such as that described in the above cited patent issued to Shoberg et al. The provision of tubing overlying the extruded tubular lead body also provides for increased protection of the conductors therein without an over-all increase in lead diameter. This use of tubing which is of increased durability and/or greater insulative strength further enhances this benefit of the lead body structure.

DETAILED DESCRIPTION OF THE PREFERRED EMBODIMENT

Figure 1:
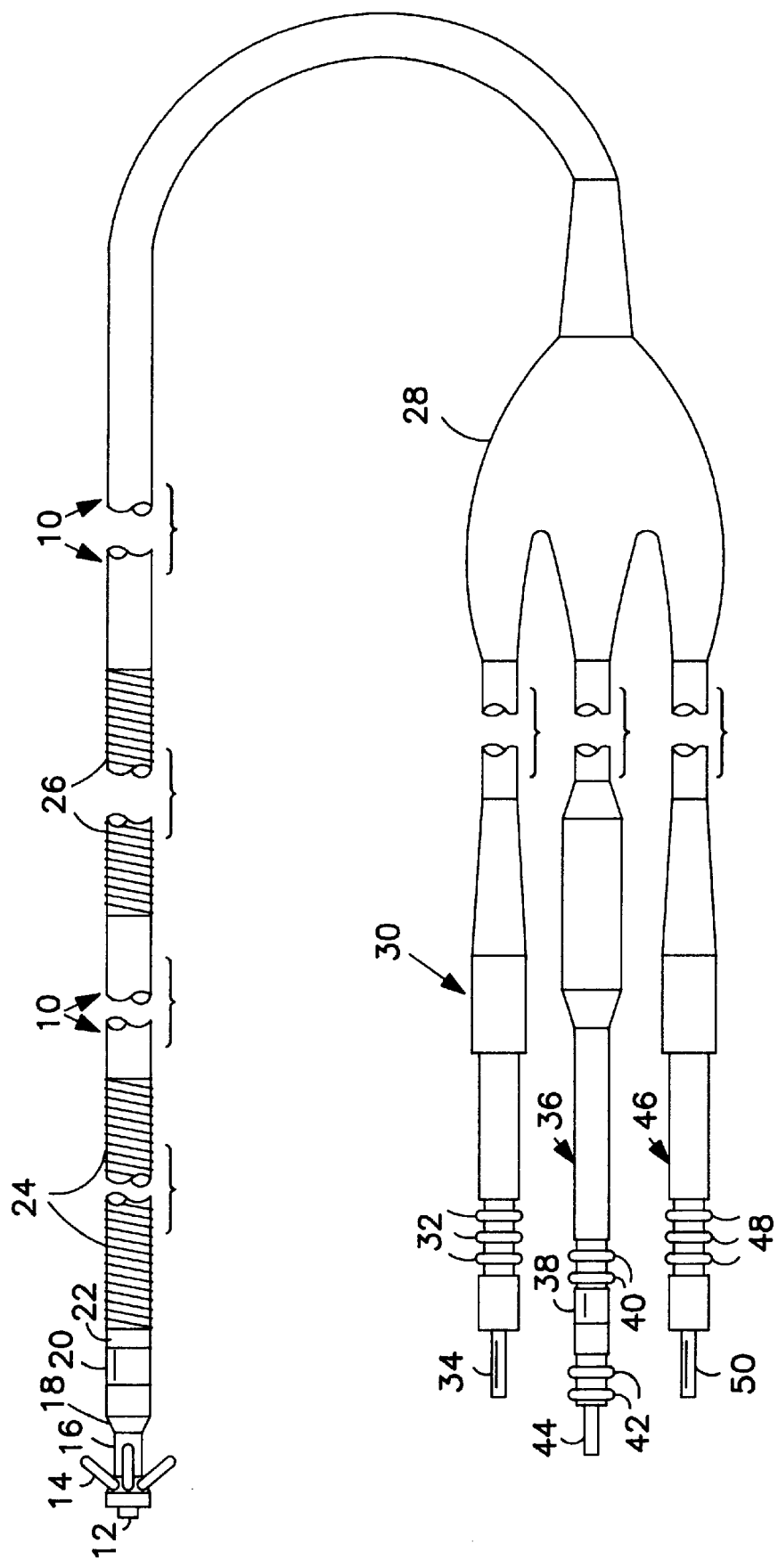
FIG. 1 is a plan view of a lead according to the present invention, provided with two coil electrodes.

FIG. 1 is a plan view of a lead according to the present invention, embodied as a transvenous cardiac defibrillation lead. The lead is provided with an elongated lead body 10 which carries four mutually insulated conductors therein, not visible in this view. Three of the insulated conductors are stranded or cabled conductors, each coupled to one of ring electrode 20, distal coil electrode 24 and proximal coil electrode 26. A fourth, coiled conductor is coupled to distal or tip electrode 12. The distal portion of the lead includes the tip-ring assembly which includes the tip or distal electrode 12, the tine sheath 16 carrying tines 14, the tip-ring spacer component 18, the ring electrode 20 and the ring-coil spacer component 22. These components together provide a generally rigid assembly, with the tine sleeve 16 fabricated of silicone rubber or relatively softer polyurethanes, and the tip-ring and ring-tip spacers 18 and 22 are fabricated of relatively harder plastics, for example polyurethane having a Shore hardness of at least 75D, to provide a relatively rigid assembly extending to the distal end of distal defibrillation electrode 24.

At the proximal end of the lead body are three connector assemblies 30, 36 and 46, extending from a molded trifurcation sleeve 28, typically formed of silicone rubber. Connector assembly 30 carries a single connector pin 34, coupled to the conductor coupled to the distal coil electrode 24, and is provided with sealing rings 32 to seal the connector assembly 30 within the connector bore of an associated implantable cardioverter/defibrillator. Likewise, connector assembly 46 is provided with a single connector pin 50 coupled to the conductor coupled to the proximal coil electrode 26, and is provided with sealing rings 48. Connector assembly 36 takes the form of an IS-1 type connector assembly provided with a connector pin 44 coupled to the coiled conductor extending to tip electrode 12 and a connector ring 38 coupled to a cabled conductor extending to ring electrode 20. Sealing rings 40 and 42 seal the connector assembly within the connector bore of an associated cardioverter/defibrillator and seal between connector pin 44 and connector ring 38. The lead body 10 which extends from the trifurcation sleeve 28 to the tip-ring assembly at the distal end of the lead is preferably formed of an extruded multi-lumen tube, formed of a plastic substantially less rigid than the ring-tip and tip-ring spacer components 18 and 22. Lead body 10 may for example be formed of silicone rubber and/or a relatively softer implantable polyurethane such as those typically employed in transvenous cardiac lead bodies. In the areas between coil electrodes 24 and 26 and in the area between coil electrode 26 and trifurcation sleeve 28, the lead body is provided with an overlay tubing having essentially the same outer diameter as coil electrodes 24 and 26, which may also be fabricated of silicone rubber, polyurethane or the like.

Figure 2:
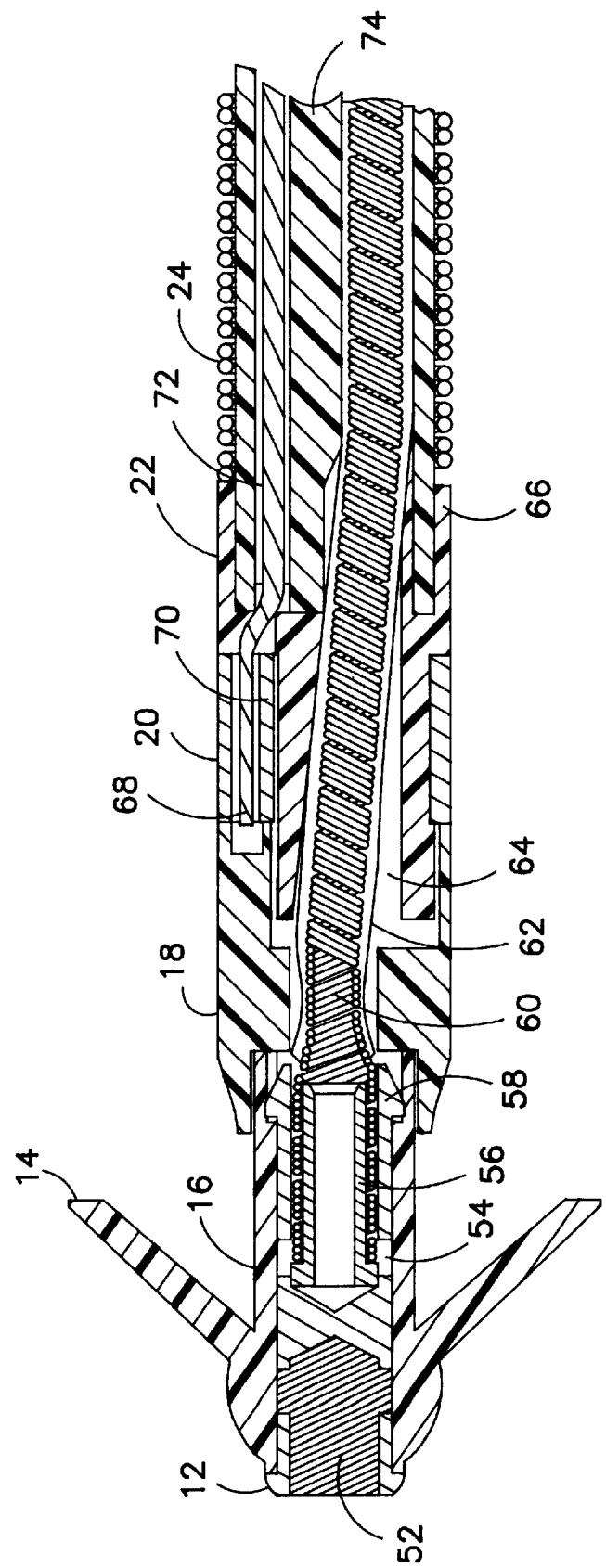
FIG. 2 is a sectional view through the distal portion of the lead illustrated in FIG. 1, illustrating the construction of the tip-ring assembly.

FIG. 2 is a sectional view through the tip ring assembly of the lead of FIG. 1. At the distal end of the assembly is the distal or tip electrode 12 which is provided with an elongated proximally extending shank around which the tine sleeve 16 is mounted. Electrode 12 may be fabricated of platinum/iridium alloy or other biocompatible metal typically used for cardiac pacing electrodes. The shank portion of electrode 12 contains a proximal facing bore in which a monolithic controlled release device 52 is located, containing an anti-inflammatory steroid such as dexamethasone compounded into a plastic matrix, for example as disclosed in U.S. Pat. No. 4,972,848 issued to DiDomenico or U.S. Pat. No. 4,506,680 issued to Stokes, both incorporated herein by reference in their entireties or as implemented in any of the various commercially available steroid eluting cardiac pacing leads.

The shank portion of the electrode 12 also contains a distally facing bore in which the distal end of coiled conductor 60 is located. The distal end of coiled conductor 60 is maintained within the shank by means of a crimping or swaging core 56, with conductor 60 compressed between the electrode 12 and the crimping or swaging core 56. Cross bores 54 are provided through the distal portion of the shank of the electrode, allowing for verification of proper placement of coiled conductor 60 during crimping. The distalmost portion of the shank of the electrode 12 includes a radially extending, distally facing flange 58 which engages with a corresponding internally directed proximally facing circumferential flange, molded into tine sleeve 16. Tine sleeve 16 is preferably fabricated of silicone rubber or a relatively softer polyurethane, for example having a Shore hardness of 80A.

Tine sleeve 16 is adhesively bonded to the tip-ring spacer component 18, for example using silicone medical adhesive or a polyurethane based adhesive, depending on the material of tine sleeve 16. Component 18 overlaps the proximal end of the shank of electrode 12 and the proximal end of tine sleeve 16. Component 18 is provided with a proximally facing internal lumen into which the portion 66 of the ring-coil spacer 22 is inserted. The tip-ring spacer and ring-coil spacer 18 and 22 together define a circumferential groove with corresponding proximal and distal facing shoulders which retain ring electrode 20, when assembled. Components 18 and 22 are preferably fabricated of a relatively more rigid plastic than the tine sleeve 16, for example of polyurethane having a Shore hardness of 75D.

A length of PTFE tubing 62 is heat shrunk around coiled conductor 60 and at least the distal portion of the outer surface thereof has been treated to render the tubing bondable, for example by etching by means of the process commercially available from Zeus Industrial Products, Inc., Orangeburg, S.C. Alternative surface treatments may also be employed to render the tubing bondable, for example using plasma etching or adhesion promoters as described in U.S. Pat. No. 4,944,088 issued to Doan et al., incorporated herein by reference in its entirety. This tubing 62 extends the over the length of the coiled conductor 60 between electrode 12 and connector assembly 36. After assembly, the unfilled space 64 within the tine sleeve 16 and tip-ring and ring-coil spacers 18 and 20 is backfilled with adhesive, bonding the components to themselves and to the etched PTFE tubing 62 and providing for mechanical interlock of all of these components to provide a generally rigid assembly extending from the distal electrode 12 to the distal coil electrode 24.

In this view it can be seen that the ring electrode 20 is provided with an inwardly extending lug 70 having a longitudinal bore into which the distal end of a stranded or cabled conductor 68 has been inserted and which is maintained therein by means of crimps applied to the lug 70. By this mechanism, and in conjunction with the adhesive and mechanical interconnection of the components of the tipring assembly shrink tube 62, tensile forces applied to the proximal end of the lead are transmitted to the tip-ring assembly, facilitating removal of the lead without breakage or partial disassembly of the distal portion of the lead.

A molded multi-lumen lead body 74 is fabricated of a material softer than the components 18 and 22, for example extruded silicone rubber, or polyurethane having a Shore, for example of 80A or 90A, or the like. Lead body 74 is inserted into a proximal facing recess within ring-coil spacer component 22, and is bonded adhesively therein, for example using a polyurethane or silicone based adhesive. The configuration of the lead body in cross-section is illustrated in more detail in FIG. 3. Coiled conductor 60 and cabled conductor 68 each extend proximal to the connector assembly through lumens in extruded lead body 74. Cabled conductor 68 as illustrated is provided with an ETFE coating 72 which is in turn bonded to the interior of the lumen of extruded lead body 74 in which it is located. At least the distal outer surface of insulation 72 is treated to render it bondable, for example using any of the mechanisms discussed above. Alternatively, the coating 72 may be ETFE which has been modified by exposure to gas plasma, for example using an apparatus as described in U.S. Pat. No. 5,364,662 issued to DiDomenico et al, also incorporated herein by reference in its entirety, with silane used as the feed gas, and ETFE as the plastic to be surface treated.

Coil electrode 24 in this view is visible as having essentially the same outer diameter as the proximal portion of the ring-coil spacer component 22, whereby an essentially isodiametric profile is maintained from the tip-ring spacer up to and including the coil electrode 24. As will be discussed further, this isodiametric profile is maintained proximal to the illustrated portion of the lead by means of overlay tubing, mounted between the electrode coils and between the proximal electrode coil and the trifurcation sleeve (not illustrated in this Figure).

Figure 3:
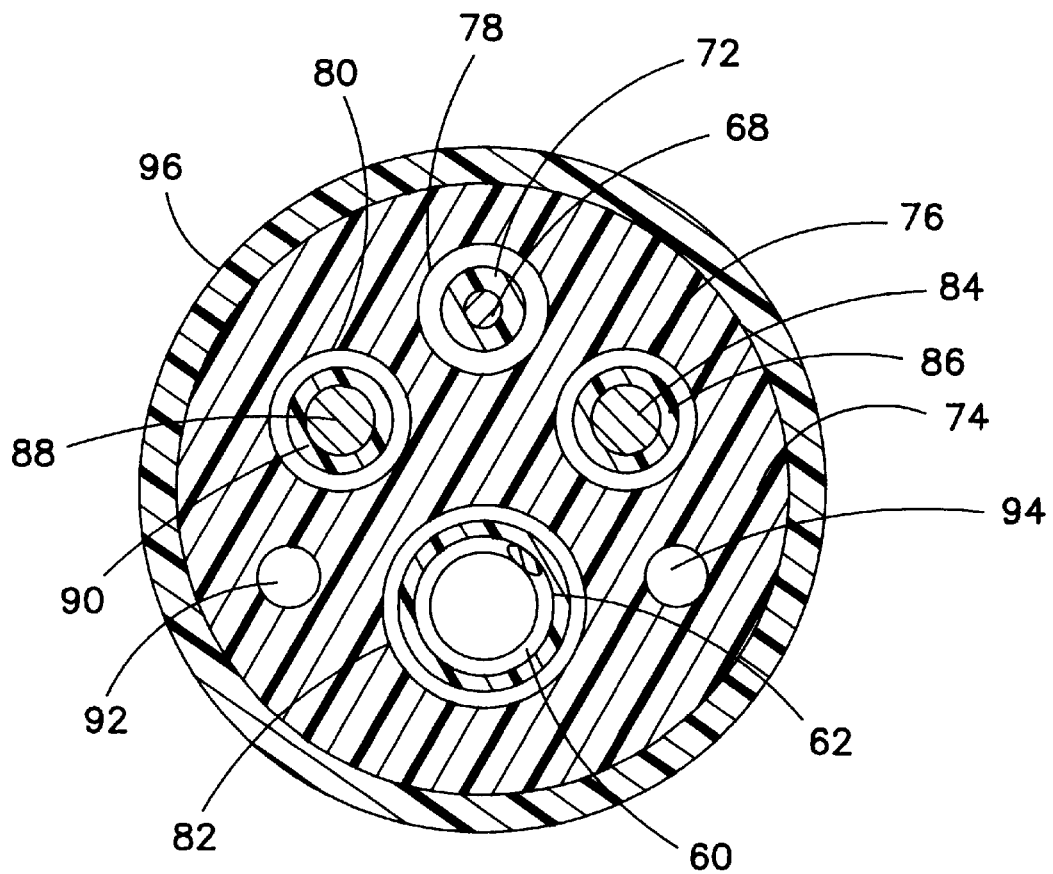
FIG. 3 is a cross-sectional view of the lead of FIG. 1, taken between the coil electrodes mounted thereon.

FIG. 3 illustrates a cross-section through the body of the lead of FIG. 1 in an area intermediate the proximal and distal electrode coils. The lead body 74 is visible in cross-section, and is provided with the total of six lumens extending therethrough, including a first lumen 82 in which the coiled conductor 60, coupled to tip electrode 12 (FIG. 2) is located. The PTFE tubing 62 surrounding coiled conductor 60 is also visible in this view. In second and third lumens 76 and 80 are located stranded conductors 84 and 88, each provided with an insulative coating, 86, 90 of ETFE. Conductors 84 and 88 couple the proximal and distal coil electrodes 24 and 26 (FIG. 1) to their associated connector pins at the proximal end of the lead. A fourth lumen 78 carries stranded or cabled conductor 68 which is coupled to ring electrode 20 (FIG. 2). PTFE coating 72, rendered bondable as discussed above by treatment with silane gas plasma or otherwise, is also visible surrounding stranded conductor 68. Compression lumens 92 and 94 are provided to enhance the ability of the lead to resist crush as described in the above cited Shoberg et al patent, and are located diametrically opposite lumens 80 and 76.

Stranded conductors 84, 88, and 68 may correspond to those described in the Shoberg et at., Williams et al. and/or Laske et al. patents cited above. The number and configuration of the individual strands within the conductor may vary as a function of the expected level of current to be carried by the conductors and as a function of the material of which they are fabricated. Typically, it is expected that in the context of a pacing/cardioversion/defibrillation lead, the conductors be fabricated of MP35N alloy wire or silver cored MP35N wire. Coiled conductor 60 may be a monofilar or multifilar coiled conductor, for example having one through five filars, and corresponds to commonly employed coiled conductors used in implantable pacing leads. The coiled conductor 60 may be also fabricated of MP35N alloy or silver cored MP35N wire.

Surrounding the outer periphery of the lead body 74 is overlay tubing 96, which has approximately the same outer diameter and the same thickness as the wire from which the coil electrodes 24 and 26 are fabricated, providing for an essentially isodiametric assembly extending from the proximal coil electrode 26 to the tip-ring assembly illustrated in FIG. 2. A corresponding second overlay tubing extends around lead body 74 proximal to coil electrode 26 (not visible in this view).

Figure 4:
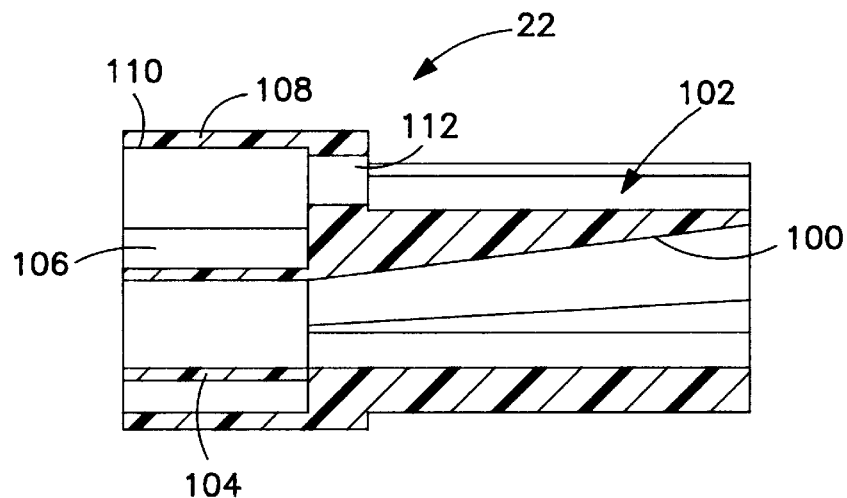
FIG. 4 is a sectional view through the ring-coil spacer component illustrated in FIG. 2.
Figure 5:
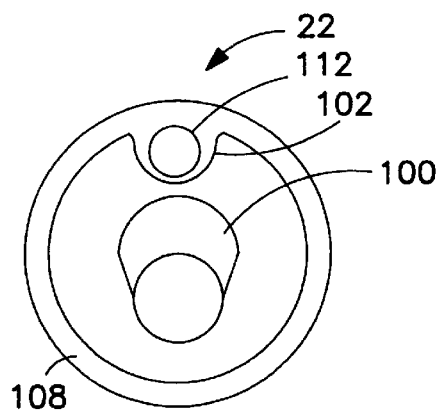
FIG. 5 is a plan view of the distal end of the ring-coil spacer component.
Figure 6:
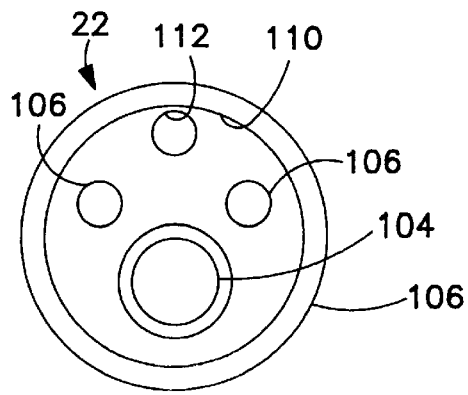
FIG. 6 is a plan view of the proximal end of the ring-coil spacer component.

FIG. 4 is a cutaway view through the ring-coil spacer 22. The orientation of the component in this figure is reversed from that in FIG. 2. The ring-coil spacer component 22 is provided with a through lumen 100, through which the coiled conductor 60 (FIG. 2). The component is additionally provided with a generally V-shaped groove 102 in which the lug 70 of the ring electrode 20 (FIG. 2) is located. The proximally facing end of the component 22 is provided with a recess 110 which receives the distal portion of the lead body 74 (FIG. 2). The recess 110 is surrounded by a circumferential wall 108 which has an outer diameter isodiametric to that of the distal coil electrode 24. Extending proximally within recess 110 is a cylindrical sleeve 104 which is inserted into lumen 82 of lead body 74 (FIG. 3). Two proximally extending pins 106 are also located within recess 110 and are configured to be inserted into lumens 80 and 76 of lead body 74 (FIG. 3). Bore 112 allows for passage of the stranded or cabled conductor 68 from the lead body 74 into the lug of the ring electrode 20 (FIG. 2). FIG. 5 is a plan view of the distal end of the ring-coil spacer 22, illustrating the relationship of the U-shaped groove 102, the bore 112, the through lumen 100 and the circumferential wall 108 in more detail. FIG. 6 is a plan view of the proximal end of the component 22, illustrating the relative locations of the circumferential wall 106, the cylindrical sleeve 104, pins 106 and bore 108, in more detail.

Figure 7:
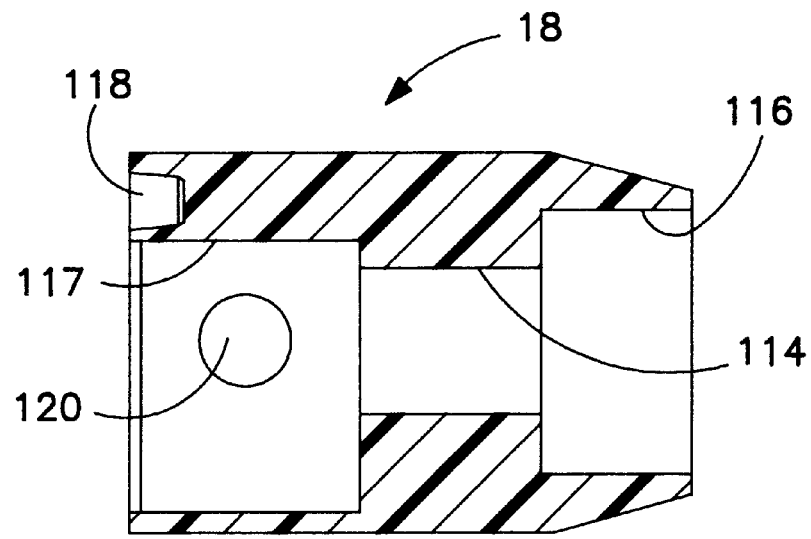
FIG. 7 is a sectional view through the tip-ring spacer component illustrated in FIG. 2.
Figure 8:
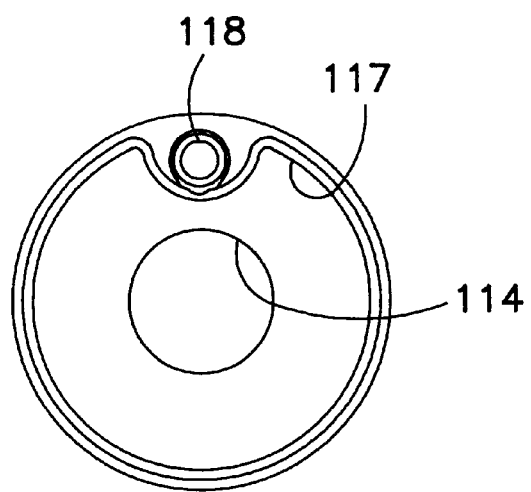
FIG. 8 is a plan view of the proximal end of the tip-ring spacer component.

FIG. 7 is a sectional view through the tip-ring spacer 18. Again, the orientation of this view is reversed from that illustrated in FIG. 2. The tip-ring spacer 18 is provided with a through lumen 114, through which the coiled conductor 60 (FIG. 2) extends. A distal-facing recess 116 receives the proximal end of the tine sleeve 16 (FIG. 2) and overlaps the proximal portion of the shank of electrode 12 (FIG. 2). A proximal facing recess 117 receives the distal portion of component 22 as illustrated in FIGS. 4–6. A small proximally facing lumen 118 is provided, which as assembled is aligned with the bore through the lug 70 of ring electrode 20 (FIG. 2), providing a recess into which the cabled or stranded conductor 68 may extend. Bores 120 are provided through the sidewall of component 18, allowing for backfilling of the recess 64 internal to the tip-ring assembly, as illustrated in FIG. 2. FIG. 8 is a plan view of the proximal end of component 18 and illustrates the configuration of the recess 117 which receives the distal portion of component 22, through lumen 114 and recess 118 in more detail.

Figure 9:
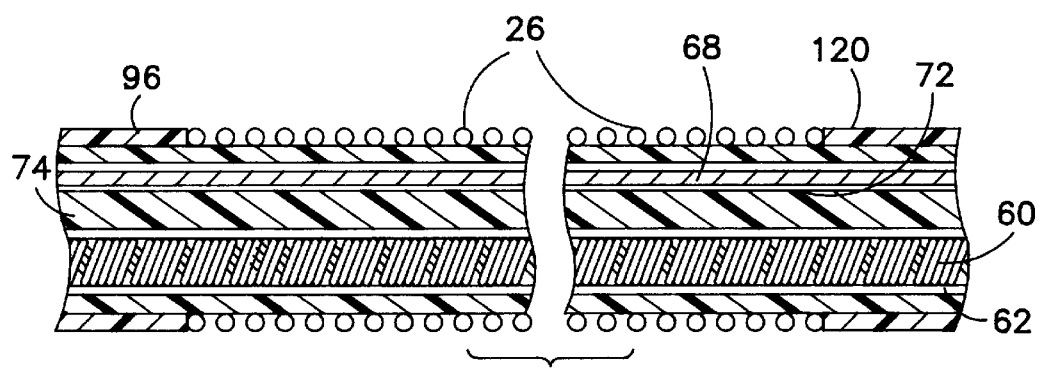
FIG. 9 is a sectional view of the lead of FIG. 1 in the vicinity of one of the coil defibrillation electrodes.

FIG. 9 is a sectional view through the lead of FIG. 1 in the vicinity of the proximal coil electrode 26. Coil electrode 26 is shown located around lead body 74, flanked on its proximal and distal ends by overlay tubing 96 and 120. Overlay tubing 96 corresponds to the same element illustrated in FIG. 3 and extends between coil electrodes 24 and 26. Overlay tubing 120 extends to the trifurcation sleeve 28, illustrated in FIG. 1. Together the coil electrodes 24 and 26 in conjunction with the overlay tubing 96 and 120 provide an essentially isodiametric lead body extending from the trifurcation sleeve to the tip-ring assembly illustrated in FIG. 2. Also visible in this view are stranded or cabled conductor 68 and associated insulative coating 72 and coiled conductor 60 and associated heat shrink PTFE tubing 62. Although not illustrated in FIG. 9 it should be understood that the coil electrodes 24 and 26 may be coupled to stranded or cabled conductors 88 and 84 (FIG. 3) by means of cross-groove crimp sleeves of the sort described in the above cited patent issued to Boser et al.

Figure 10:
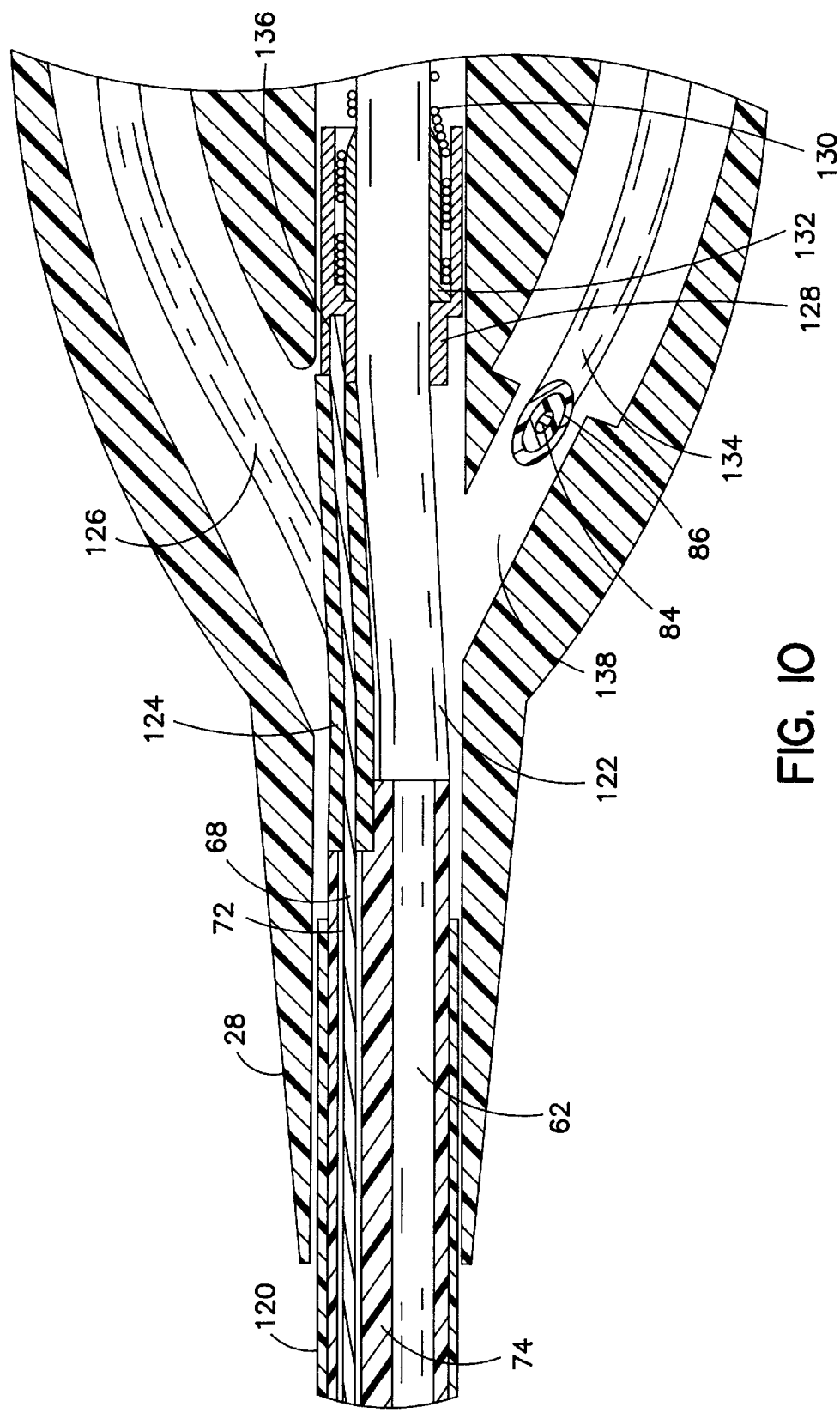
FIG. 10 is a cutaway view of a portion of the lead of FIG. 1 adjacent the connector assemblies.

FIG. 10 illustrates a cutaway view through the lead of FIG. 1 in the vicinity of trifurcation sleeve 28. Lead body 74 enters the distal end of trifurcation sleeve 28 and terminates therein. Stranded or cabled conductor 68 extends through lead body 74, out its proximal end and through spacer tubing 124 which extends to transition flange 128, which in turn contains a bore 136 in which the proximal end of cabled or stranded conductor 68 is crimped. At least the proximal outer surface of ETFE insulative coating 72 applied to conductor 68 is made bondable using one of the methods discussed above and as adhesively bonded to the lumen of lead body 74, in the area adjacent to the point at which it exits lead body 74. This adhesive bond provides for a mechanical interconnection between the conductor 68 and the lead body 74, in region of the trifurcation sleeve, which in turn enhances the ability to transmit tensile force provided by the mechanical and electrical interconnection of the stranded or cabled conductor 68 to transition sleeve 128. A coiled conductor 130 is coupled to transition sleeve 128 by means of a crimping or swaging core 132. Connector 130 extends proximally to the IS-1 connector assembly 36 (FIG. 1) where it is coupled to connector ring 38 in a conventional fashion.

Also visible in this view is PTFE shrink tubing 62 which surrounds the coiled conductor 60 (FIG. 2). Shrink tubing 62 and conductor 60 extend proximally inside inner tubing 122 which also extends proximally to the IS-1 connector assembly 36. As discussed below, PTFE shrink tubing 62 is adhesively bonded to the interior of inner tubing 122, in the vicinity of IS-1 connector 36, further enhancing the ability of the lad to transmit tensile force from the proximal to the distal tip of the lead. Also visible in this view are two insulative tubes 126 and 134, each of which surrounds one of the stranded conductors coupled to a coil electrode, and which extend back to the connector assemblies 30 and 46, illustrated in FIG. 1. Tube 134, for example, carries conductor 84 and associated insulative coating 86. The recess 138 defined within trifurcation sleeve 28 is backfilled with silicone rubber medical adhesive, providing a mechanical interconnection of all the components therein. This mechanical interconnection also assists in mechanically coupling the proximal end of the lead body to IS-1 connector assembly 36 and trifurcation sleeve 28.

Figure 11:
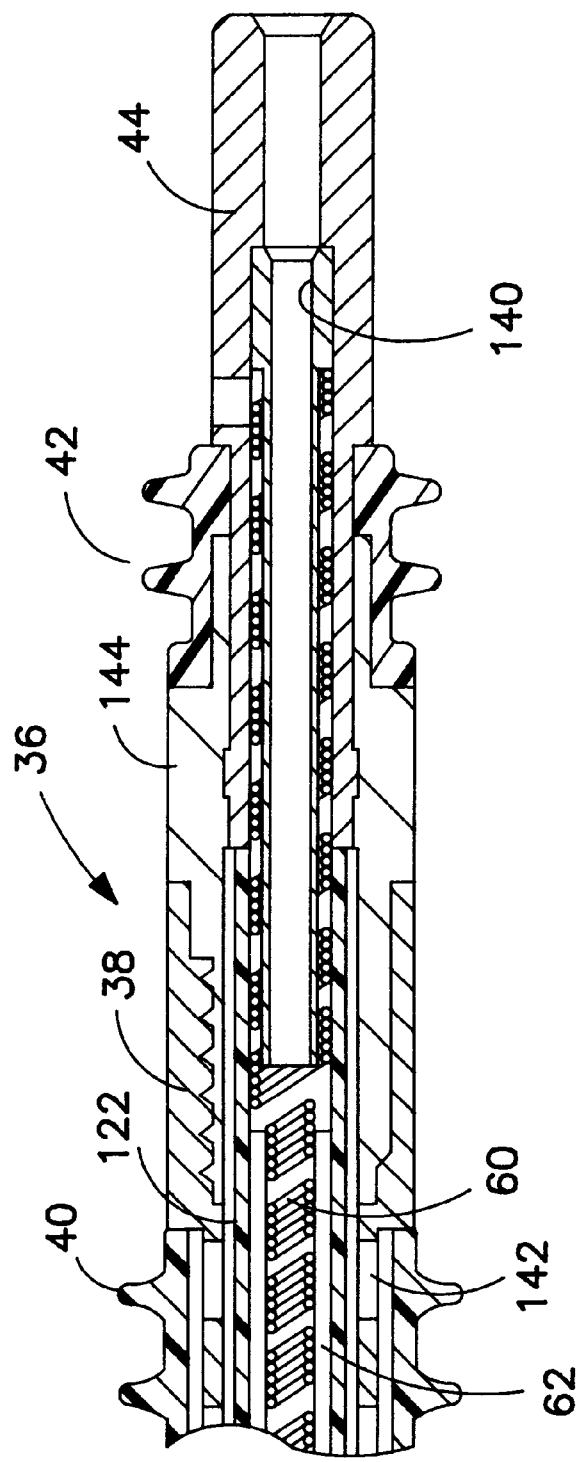
FIG. 11 is a sectional view through a portion of one of the connector assemblies of the lead of FIG. 1.

FIG. 11 is a cutaway view through IS-1 connector assembly 36, illustrating the interconnection of the various components including the connector ring 38, connector pin 44 and sealing rings 40 and 42. As illustrated, coiled conductor 60 is coupled to connector pin 44 by means of a crimping or swaging core 140. Coiled conductor 60 and its associated PTFE shrink tubing 62 are located within inner tubing 122, which extends proximally from trifurcation sleeve 28, as illustrated in FIG. 10. Ring electrode 38 is provided with cross bores 142 which facilitate backfilling of the recess between the ring electrode 38 and the inner tubing 122, serving to mechanically interconnect the inner tubing 122 to ring electrode 38 and sealing rings 40. Ring electrode 38 is in turn mechanically interconnected with connector pin 44 by means of injection molded spacer 144, fabricated according to U.S. Pat. No. 4,572,605 issued to Hess, incorporated herein by reference in its entirety. At least the proximal outer surface of PTFE shrink tubing 62 applied to conductor 60 is made bondable using one of the methods discussed above and is adhesively bonded to the lumen of inner tubing 122, further facilitating transmission of tensile forces from the proximal end to the distal end of the lead body, as discussed above.

The above disclosed embodiment of a lead according to the present invention takes the form of a cardioversion/defibrillation lead which is provided with four electrodes including a tip electrode, a ring electrode and two defibrillation electrodes and which employs all three of the described extraction enhancing features in combination. Variations of the invention, using one or more of the features enumerated herein particularly adapted to assist in rendering the lead extractable, may of course be used in conjunction with leads having a greater or fewer number of electrodes and conductors. As such, the above disclosure should be considered exemplary, rather than limiting, with regard to the claims which follow.

In conjunction with the above specification, we claim:

1. A medical electrical lead comprising:

an elongated plastic tube having proximal and distal ends;

first and second elongated conductors mounted in said plastic tube; and a tip-ring assembly mounted to the proximal end of the tube, the tip-ring assembly comprising:

a ring electrode coupled to the first conductor;

a tip electrode located distal to the ring electrode and coupled to the second conductor; and two molded plastic components separately fabricated of a plastic harder than the plastic tube, adhered to one another and together defining a circumferential groove in which the ring electrode is located, a more distally located one of the molded plastic components mechanically coupled to the tip electrode.

2. A lead according to claim 1 wherein the tip electrode comprises a proximally extending electrode shank and further comprising a tine sleeve fabricated of a plastic softer than the molded plastic components and mounted around said electrode shank.

3. A lead according to claim 2 wherein the more distally located one of the molded plastic components is adhered to the tine sleeve.

4. A lead according to claim 3 wherein the more distally located molded plastic component overlaps the electrode shank.

* * * * *